United States Patent
Liang et al.

(10) Patent No.: US 11,640,853 B2
(45) Date of Patent: May 2, 2023

(54) PERSONAL HEALTH RECORD SYSTEM WITH PROCESS DECISION SUPPORT FUNCTION

(71) Applicant: Yueqiang Liang, Jiangsu (CN)

(72) Inventors: Yueqiang Liang, Jiangsu (CN); Dengwang Li, Shandong (CN); Chuanyi Zhang, Shandong (CN)

(73) Assignee: Yueqiang Liang, Suzhou (CN)

( * ) Notice: Subject to any disclaimer, the term of this patent is extended or adjusted under 35 U.S.C. 154(b) by 381 days.

(21) Appl. No.: 16/474,328

(22) PCT Filed: Dec. 25, 2017

(86) PCT No.: PCT/CN2017/118335
§ 371 (c)(1),
(2) Date: Jun. 27, 2019

(87) PCT Pub. No.: WO2018/126925
PCT Pub. Date: Jul. 12, 2018

(65) Prior Publication Data
US 2019/0348161 A1    Nov. 14, 2019

(30) Foreign Application Priority Data
Jan. 4, 2017    (CN) .......................... 201710003548.5

(51) Int. Cl.
*G16H 10/60*    (2018.01)
*G16H 50/20*    (2018.01)

(52) U.S. Cl.
CPC ............. *G16H 10/60* (2018.01); *G16H 50/20* (2018.01)

(58) Field of Classification Search
CPC ............................ G16H 10/60; G16H 50/20
See application file for complete search history.

(56) References Cited

U.S. PATENT DOCUMENTS

| | | | | |
|---|---|---|---|---|
| 2006/0111943 A1* | 5/2006 | Wu | ........................ | G06Q 10/10 705/2 |
| 2012/0215560 A1* | 8/2012 | Ofek | ...................... | G16H 10/00 705/3 |
| 2016/0354039 A1* | 12/2016 | Soto | ........................ | A61B 5/74 |

FOREIGN PATENT DOCUMENTS

| | | |
|---|---|---|
| CN | 103116643 A | 5/2013 |
| CN | 105975783 A | 9/2016 |
| CN | 106156492 A | 11/2016 |
| CN | 105912881 B | 12/2018 |

* cited by examiner

Primary Examiner — Jay M. Patel (57) ABSTRACT

The present invention discloses a personal health record system with a process decision support function. By constructing a personal health record system with separated characteristic data extraction and characteristic data analysis, characteristic data that meets analysis requirements is expected to be rapidly obtained. A statistics query interface based on characteristic data and time logic is provided, and decision support for users is completed through steps such as characteristic matching, process classification and statistics evaluation, and process recommendation, so as to make medical big data better execute high-level information analysis and decision support functions.

10 Claims, 1 Drawing Sheet

PERSONAL HEALTH RECORD SYSTEM WITH PROCESS DECISION SUPPORT FUNCTION

FIELD OF THE INVENTION

The present invention relates to medical big data.

BACKGROUND OF THE INVENTION

With the rapid development of medical information technology and computer technology, various forms of medical health information systems such as Electronic Medical Record (EMR), Electronic Health Record (EHR), and Personal Health Record (PHR) systems accumulate a great amount of data. Computer-aided diagnosis and treatment plan recommendation systems emerge as the times require. The determination of traditional disease diagnosis and treatment plans depends on the professional competence of doctors and their knowledge of disease-related expertise. Comparatively, the computer-aided diagnosis and treatment plan recommendation systems are featured in strong memory and information integration ability and so on, thereby reducing the misdiagnosis rate and improving the efficiency.

Up to now, many computer systems have been developed for assisting in diagnosis and treatment plan selection, such as "DxPlain", "Isabel" and "Dr. Watson".

The DxPlain system from Massachusetts General Hospital can search for reliable medical evidences and synonyms in its knowledge base according to user input information to find matched items. Finally, DxPlain lists various possible diagnoses according to symptoms, physical examination, examination results, and various other factors of patients.

The Isabel system provides doctors with an online list, and makes an accurate diagnosis after symptoms and examination results are inputted, mainly for preventing doctors from neglecting possible rare diseases and causing misdiagnosis.

However, both DxPlain and Isabel perform decision support based on a knowledge base, and they do not have the ability to obtain feedback directly from a large amount of patient data.

The "Dr. Watson", developed by IBM, uses AI technology, advanced natural language processing and analysis technology to simulate the human learning process and acquire knowledge based on massive data collected from various channels (including medical journals, textbooks, and information collected from doctors or hospitals using the system). It can give "opinions" quickly and guide doctors to make diagnosis and treatment decisions. However, the natural language understanding technology itself is very complex, and the technology that can be deeply understood in combination with the context is still immature.

Patent (application number: 201610416289.4) has disclosed a personalized treatment plan recommendation system based on a big data knowledge base. By matching the personal information and disease condition information of the patient with the personal information and disease condition information in the knowledge base, it acquires the treatment plan with the highest treatment effect score and recommends it to the user. It can obtain feedback from the accumulated case data through the treatment effect score. However, this patent requires each case entering the knowledge base to be scored in terms of the treatment effect, and recommends the individual case treatment plan with the highest treatment effect score to the user. It is prone to make incorrect treatment plan recommendations because of unrepresentative individual cases.

Another problem facing medical big data is the challenge of unstructured data. Unstructured data contains a lot of information about disease condition or treatment, which, however, needs to be extracted with complex technology. At the same time, not all structured data can be used for analysis to produce significant results. Data for analysis must has clear and consistent definitions. In the summary below, we define characteristic data for analysis.

On the other hand, the modern clinical decision support system should consider not only the current health condition of the patient, but also the health and treatment history of the patient as well as its dynamic changes. These all involve an important factor: time. Usually, the expression of time in the clinical decision support system can be divided into three kinds: time point, time period, and time length. A time point represents a moment with a time length of zero, such as 0:00 on Dec. 3, 2016 (values corresponding to time units smaller than hour are all 0 and omitted). A time period consists of a start time point and an end time point. The end time point minus the start time point is the time length of the time period. Time period is a vector on the time axis, which has a start point and an end point, and also has a time length, such as from 0:00 on Dec. 3, 2016 to 0:00 on Dec. 7, 2016. A time length is a scalar quantity, which has no start point or end point, such as one hour and two days.

Personal Health Record (PHR) is a file that records all changes in vital signs from birth to death of each person, as well as all health-related behaviors and events that he or she has engaged in. Specific content mainly comprises living habits, past medical history, diagnosis and treatment situations, family medical history, current medical history, and examination results of each person, as well as occurrence, development, treatment, and prognosis process of diseases, etc. Compared with EMR and EHR systems maintained by hospitals, PHR systems are oriented to patients allowing the patients to master their own health information, and they are regarded as an important development direction of medical data information systems.

SUMMARY OF THE INVENTION

The present invention discloses a personal health record system with a process decision support function, which consists of a server and a client. The client of the system can be a desktop workstation, a notebook computer, a tablet computer, a smart phone, or other smart hardware; and the server of the system is a data storage, calculation, and analysis platform located in the cloud.

In medical statistics analysis, data variables are classified into two types, one type is numerical variables and the other type is classification variables. Here, for ease of description, we define those numerical variables and classification variables, which reflect user information or process information, are clinically significant, and have clear and consistent definitions, as characteristic data. Quantitative data has clear and consistent data meanings, value ranges, and units. Classification data has clear and consistent classification criteria and type set definitions. User characteristic data comprises basic information, symptoms, signs, and inspection and examination results of users, clinically significant characteristics extracted from images, voices, videos, and waveform data of users, and all quantitative or classification data which reflects attributes or physical states of users. Process characteristic data comprises clinically significant examination data, treatment data, environmental data, and all quantitative or classification data which reflects operations or environments acting on users. The process here refers to the diagnostic and therapic operations or environments acting on patients.

Differing from the organization form for structured data to define data, characteristic data defines the type of data itself. Typical user characteristic data comprises gender (classification variable), height (numerical variable), white blood cell count (numerical variable), mass volume (numerical variable), whether there is a headache (classification variable), cancer TNM staging (classification variable), etc. Typical process characteristic data comprises main magnetic field intensity of magnetic resonance imaging (numerical variable), injection dose of a certain medicine (numerical variable), whether IR lymph nodes are cleared during lung cancer surgery (classification variable), etc.

Other data except characteristic data is referred to here as non-characteristic data. Typical non-characteristic data comprises patient name, native place information with undefined format and level of specificity, images, waveforms, videos, disease condition text description, etc.

Whether data is characteristic data mainly depends on whether the data has clinical significances and whether the data has clear and consistent definitions. Patient name is not characteristic data in the sense of distinguishing individual patients, because different patients may have the same name. Patient ID, as a distinct and unique marker of each patient, is classification characteristic data to distinguish individual patients. Patient name may also indicate a classification of patients with the same name. In this sense, patient name has clear and consistent definitions, but it is uncertain whether it has clinical significances.

Some of characteristic data of users, such as height and blood type, may be inputted directly by users or read from other systems such as EMR, EHR, and PHR. Some needs to be extracted from non-characteristic data, such as by drawing masses on CT images (non-characteristic data) and calculating volumes of the masses (characteristic data).

However, there are various types of non-characteristic data, and there are various ways to extract characteristic data from non-characteristic data. In order to extract characteristic data from non-characteristic data more effectively for process recommendation, the server of the present invention comprises a non-characteristic data processing interface. The non-characteristic data processing interface comprises a non-characteristic data query interface, an interface for acquiring non-characteristic data from the personal health record system, and an interface for transmitting characteristic data extracted from the non-characteristic data and newly generated non-characteristic data back to the personal health record system. In addition, the non-characteristic data processing interface may also comprise a user authorization interface and a service purchase interface according to the needs. The user authorization interface ensures that data acquired through the non-characteristic data processing interface is authorized by data owners. Authorization protocols may adopt OAuth 2.0, SAML, CAS, OIDC, etc. The service purchase interface may allow users to pay for paid characteristic extraction services. The service purchase interface may be connected to a third-party payment platform, such as Alipay, Tenpay, 99Bill, Internet banking online payment and so on.

This system only limits the communication between the non-characteristic data processing side and the personal health record system to conform to the specific application program interface, and does not limit the form of characteristic extraction performed by the non-characteristic data processing side. The process of the non-characteristic data processing side extracting characteristic data may be completed by computer calculation, jointly by computer calculation and manual work, or completely by manual work.

By handing over a wide variety of characteristic data extraction work to a third party by means of providing interfaces, the extraction of a great amount of complex characteristic data is decentralized and the extraction forms are diversified, making users become the main body of this activity and be responsible for selecting characteristic data extraction providers, evaluating the characteristic data extraction quality, and paying to the characteristic data extraction providers, so as to expect to more rapidly create characteristic data that meets analysis requirements.

When receiving user characteristic data and process execution characteristic data, the system has to simultaneously receive user characteristic data and real world time corresponding to process execution. In this system, the corresponding real world time is divided into two types: effective time and observation time. Both effective time and observation time are time periods with start time and end time. The time corresponding to process execution in the real world is effective time. For example, when intravenous drip process execution characteristic data is recorded, corresponding intravenous drip time is effective time. The time corresponding user characteristic data in the real world is effective time or observation time. For example, when a user who has a headache for 5 days inputs characteristic data indicating whether there is a headache, the input time is from Dec. 1, 2016 to Dec. 5, 2016, which is the effective time of the characteristic data. For another example, when a user without a headache is asked by a doctor if he or she has a headache this week, and inputs characteristic data indicating whether there is a headache, if NO is inputted and the input time is from Dec. 1, 2016 to Dec. 7, 2016, because in fact the time without a headache is much longer than a week, this time is the observation time of the characteristic data. For example, when white blood cell count characteristic data is inputted, the corresponding time is the time of blood collection, which is also the observation time of the characteristic data. Effective time is the corresponding effective time of the characteristic data in the real world. Effective time can be directly used in time logic operations related to characteristic data. Observation time is second-best time data acquired when it is inconvenient to acquire the effective time, and cannot represent the effective time corresponding to the characteristic data in the real world. Before performing time logic operations related to characteristic data, it is required to convert the observation time into the corresponding effective time for logic operations.

The server of the system comprises a statistics query interface based on characteristic data and time logic, and the client comprises a corresponding statistics query module. The statistics query interface comprises corresponding statistics query rules.

Through the above mechanism, one part of the characteristic data in the system comes from direct user input, including manual input as well as input from other systems such as EMR or intelligent hardware devices; and the other part comes from non-characteristic data. Therefore, in this system, the process decision support module based on a characteristic data statistics model can make use of more abundant characteristic data to perform process decision support. This module executes the following three steps:

1) Characteristic matching, i.e., matching current characteristic data with a great amount of recorded case characteristic data in the system to acquire a matched case set. The characteristic data for matching is usually based on abnormal user characteristic data, and may also comprise necessary non-abnormal user characteristic data and necessary process characteristic data. That the characteristic data for matching can be individually configured means that for a group of abnormal characteristic data, the corresponding other characteristic data participating in the matching, the method for matching the characteristic data, and the measures and indexes to measure whether the characteristic data is matched all can be individually configured.

2) Process classification and statistics evaluation, i.e., classifying the matched case set according to processes to be further adopted, and performing statistics evaluation on each process classification. The processes to be further adopted refer to examinations to be further adopted, treatments, or environmental changes affecting users under the situation that the matched characteristic data is known. That the indexes for evaluation can be individually configured means that for a set of matched characteristic data and processes, different evaluation indexes can be individually configured for statistics evaluation.

3) Process recommendation, i.e., generating a recommended process list according to classification evaluation results and recommendation rules. That the recommendation rules can be individually configured means that for a group of matched characteristic data and processes, the ranking indexes, the ranking method, and the display rules of the recommended process list can be individually configured.

The present invention has the following beneficial effects: by constructing a personal health record system with separated characteristic data extraction and characteristic data analysis, characteristic data that meets analysis requirements is expected to be rapidly obtained, so as to make medical big data better execute high-level information analysis and decision support functions. The process decision support system of the present invention does not require an artificial intelligence system to collect and recognize textual data, but uses the characteristic data provided by each user and the characteristic data extracted from the non-characteristic data for statistics analysis, so as to provide feedback regarding the treatment effect, making the recommended processes more objective and accurate.

DETAILED DESCRIPTION OF THE EMBODIMENTS

In this embodiment, a personal health record system with a decision support function consists of a client and a server, wherein the client is a smart phone and a Web front-end page and a program running on the smart phone; and the server is a computer server capable of accessing, calculating, and analyzing data.

The client comprises different modules according to different roles of users. In this embodiment, the client of users of all roles comprises a statistics query module, a user information input module, a new user characteristic data module, a new non-characteristic data module, a new process module, a user characteristic data input module, a user non-characteristic data input module, a process decision support module, a process planning module, and a process execution module. The client of administrator users further comprises a module for managing user information, user characteristic data, user non-characteristic data, and process data.

Figure 1:
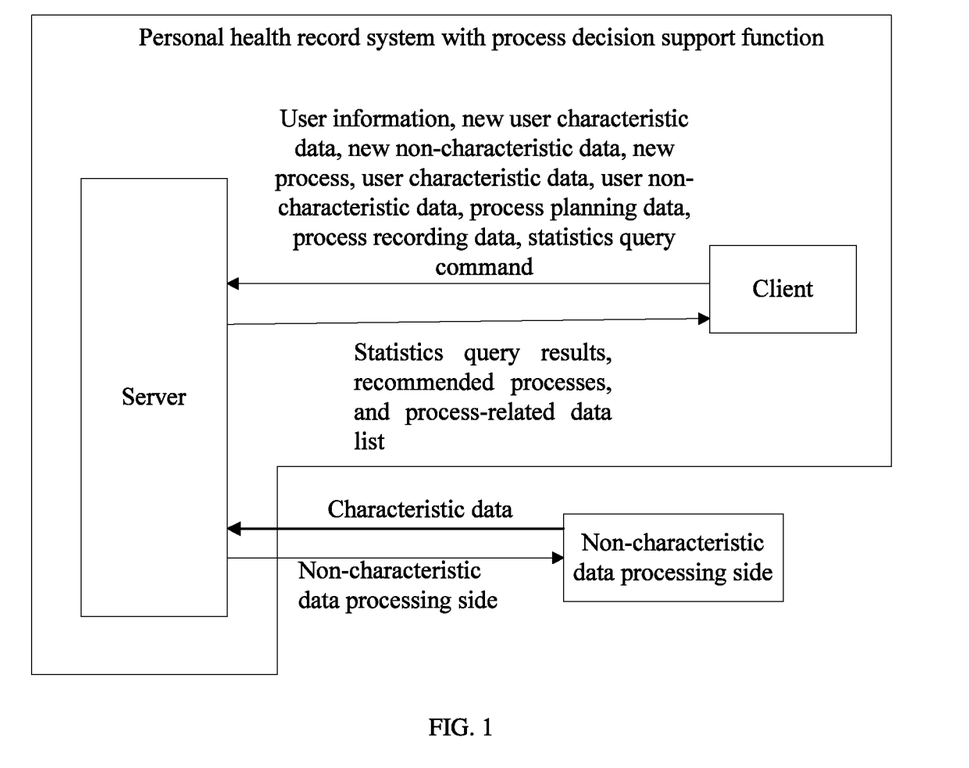
FIG. 1 illustrates a data flow diagram of a system.

The data flows of the client and the server are as illustrated in FIG. 1. The client transmits the acquired user information, new user characteristic data, new non-characteristic data, new process, user characteristic data (and corresponding real world time), user non-characteristic data, process planning data, process recording data (and corresponding real world time), and statistics query commands to the server, and the server stores them in a database. The server transmits statistics query results, recommended processes, and process-related data lists back to the client.

The statistics query module of the client is used for querying data with specified conditions and performing statistics analysis on query results, and comprises an identifier input control, an identifier adding button, a query condition input control, a return data input control, a query condition adding button, a calculation expression input control, a calculation expression result display control, a calculation expression adding button, an execution button, and a query result list, wherein the identifier input control inputs query-related identifiers; the identifier adding button can add an identifier input control; the query condition input control inputs query conditions; the return data input control inputs data items that need to be returned from eligible cases; the query condition adding button can add a group of query condition input controls and return a data input control; the calculation expression input control inputs expressions that need to be calculated; the calculation expression result display control displays calculation results of calculation expressions after executing a query; the calculation expression adding button can add a group of calculation expression input controls and calculation expression result display controls; the execution button executes a query and calculates expression results after being clicked; and the query result list displays a list of results that meet each query condition.

The completion of query and statistics depends on the statistics query interface based on characteristic data and time logic of the server. The statistics query interface in this embodiment consists of statistics query commands, operators, time functions, and statistics functions.

The operators in this embodiment comprise:
Assignment operator: "=", wherein the operation object on the left of "=" is an identifier, and the operation object on the right thereof may be value-type characteristic data, may be time periods with logic values or simple logic values, or may be time points or time lengths.

Arithmetic operators: addition "+", subtraction "−", multiplication "*", and division "/", the operation objects of which may be value-type characteristic data, or may be time points or time lengths, and the return type and the operation object type are the same.

Comparison operators: equal to "==", greater than ">", smaller than "<", greater than or equal to ">=", smaller than or equal to "<=", and not equal to "< >". When the operation object is characteristic data, the return type is real world time that meets the condition (i.e., the logic value is true); and when the operation object is a time period or time length, the return type is a simple logic value.

Logic operators: logic AND "&&", logic OR "11", logic NOT "!". When the operation object is a simple logic value, the return type is also a simple logic value; and when the operation object is a time period with a logic value, the return type is also a time period with a logic value.

The time functions in this embodiment comprise: StartTime, which represents the start time of the current matching time period; EndTime, which represents the end time of the current matching time period; and Duration (start, end), which represents a time period generated through the start time and end time.

The statistics functions in this embodiment comprise: Count (condition), which represents the number of time periods matched under specific conditions; SumInterval (condition), which represents a sum of the time lengths of the time periods matched under specific conditions; MediumInterval (condition), which represents a median time length of the time periods matched under specific conditions; and Avg(condition, numerical type characteristic data), which represents averaging the specified numerical type characteristic data of all time periods matched under specific conditions. These statistics functions all perform statistics operations for matched results.

The statistics query command in this embodiment consists of an identifier definition, a conditional expression, and a return data list. The server executes statistics query operations according to the received statistics query command. If a user simultaneously suffering from restlessness, insomnia, and dry mouth for more than a week is queried, the statistics query command is as follows: identifier 1: state 1=(mental state=restlessness && sleeping state=insomnia && salivary secretion=dry mouth) condition 1: EndTime(state 1)−StartTime(state 1)>1 week return data: user name, user ID, StartTime(state 1), EndTime(state 1); the identifier here represents the a time period during which restlessness, insomnia, and dry mouth (logic value is true) simultaneously occur; and the condition here represents that the end time of all of the above time periods minus the start time is required to be greater than one week. The return data defines values that need to be returned for time periods meeting the above conditions.

The following is an example of querying patients with alpha-fetoprotein content greater than 25 µg/l and positive hepatitis B surface antigen in two years based on the above query results, and performing relevant statistics calculation. The identifier adding button is clicked for three times to generate 3 new identifier input controls, in which the following contents are respectively inputted: state 2=(alpha-fetoprotein >25 µg/l); state 3=(hepatitis B surface antigen=positive); state 4=Duration(StartTime(state 2)−3 days, EndTime(state 2)+3 days) && Duration(StartTime (state 3)−15 days, EndTime(state 3)+15 days). Here, the observation time of alpha-fetoprotein is extended forward and backward respectively for 3 days as the effective time of alpha-fetoprotein data; the observation time of hepatitis B surface antigen is extended forward and backward respectively for 15 days as the effective time of hepatitis B surface antigen data; and the state 4 is an intersection of the effective time of alpha-fetoprotein >25 µg/l and the effective time of hepatitis B surface antigen=positive. The condition adding control is clicked to generate a condition 2 input control. Condition 2: condition 1 && StartTime(state 4)−StartTime (state 1)<2 && StartTime(state 4)−StartTime(state 1)>0 return data: user name, user ID, StartTime(state 4), EndTime (state 4). For query by condition 2, on the basis of satisfying condition 1, it is required to simultaneously satisfy that the start time of state 4 is later than the start time of state 1, and the time period by which the start time of state 4 is later than the start time of state 1 cannot exceed 2 years. In other words, patients with alpha-fetoprotein content greater than 25 µg/l and positive hepatitis B surface antigen in two years are queried on the basis of satisfying condition 1. The data in the following table is taken as an example:

| User name | User ID | Characteristic data name | Characteristic data value | Characteristic data unit | Start time | End time | Time type |
|---|---|---|---|---|---|---|---|
| Zhang Yi | 45791 | Metal state | Restlessness | | 05:00:00, May 1, 2013 | 00:00:00, July 15, 2013 | Effective time |
| | | Sleeping state | Insomnia | | 20:00:00, May 1, 2013 | 00:00:00, July 15, 2013 | Effective time |
| | | Salivary secretion | Dry mouth | | 05:00:00, May 1, 2013 | 00:00:00, May 10, 2013 | Effective time |
| | | Alpha-fetoprotein | 30 | µg/l | 13:21:00, May 3, 2016 | 13:21:15, May 3, 2016 | Observation time |
| | | Hepatitis B surface antigen | Positive | | 09:19:00, May 3, 2016 | 09:19:15, May 3, 2016 | Observation time |
| Li Er | 34861 | Metal state | Restlessness | | 05:00:00, May 7, 2014 | 00:00:00, August 15, 2014 | Effective time |
| | | Sleeping state | Insomnia | | 20:00:00, May 7, 2014 | 00:00:00, August 15, 2014 | Effective time |
| | | Salivary secretion | Dry mouth | | 05:00:00, May 7, 2014 | 00:00:00, May 20, 2014 | Effective time |
| | | Alpha-fetoprotein | 10 | µg/l | 09:18:00, May 3, 2015 | 09:18:15, May 3, 2015 | Observation time |
| | | Hepatitis B surface antigen | Positive | | 09:19:00, May 3, 2015 | 09:19:15, May 3, 2015 | Observation time |
| Zhang San | 29845 | Metal state | Restlessness | | 05:00:00, May 15, 2014 | 00:00:00, August 15, 2014 | Effective time |

-continued

| User name | User ID | Characteristic data name | Characteristic data value | Characteristic data unit | Start time | End time | Time type |
|---|---|---|---|---|---|---|---|
| | | Sleeping state | Insomnia | | 20:00:00, May 15, 2014 | 00:00:00, August 15, 2014 | Effective time |
| | | Salivary secretion | Dry mouth | | 05:00:00, May 15, 2014 | 00:00:00, May 30, 2014 | Effective time |
| | | Alpha-fetoprotein | 9 | μg/l | 09:18:00, May 3, 2016 | 09:18:15, May 3, 2016 | Observation time |
| | | Hepatitis B surface antigen | Positive | | 09:19:00, May 3, 2016 | 09:19:15, May 3, 2016 | Observation time |
| Li Si | 55465 | Metal state | Restlessness | | 05:00:00, May 5, 2014 | 00:00:00, August 15, 2014 | Effective time |
| | | Sleeping state | Insomnia | | 20:00:00, May 5, 2014 | 00:00:00, August 15, 2014 | Effective time |
| | | Salivary secretion | Dry mouth | | 05:00:00, May 5, 2014 | 00:00:00, May 30, 2014 | Effective time |
| | | Alpha-fetoprotein | 50 | μg/l | 09:18:00, March 3, 2016 | 09:18:15, March 3, 2016 | Observation time |
| | | Hepatitis B surface antigen | Positive | | 09:19:00, March 3, 2016 | 09:19:15, March 3, 2016 | Observation time |
| Wang Wu | 32984 | Metal state | Restlessness | | 09:00:00, May 1, 2014 | 13:21:15, May 3, 2014 | Effective time |
| | | Sleeping state | Normal | | 00:00:00, April 3, 2014 | 09:19:15, May 3, 2014 | Observation time |
| | | Salivary secretion | Dry mouth | | 09:00:00, May 1, 2014 | 09:19:15, May 3, 2014 | Effective time |

In the above table, Zhang Yi, Li Er, Zhang San, and Li Si all satisfy condition 1, and only Li Si satisfies condition 2. Therefore, after clicking the execution button, the query result list respectively displays query results for condition 1:

| User name | User ID | Start time | End time |
|---|---|---|---|
| Zhang Yi | 45791 | 20:00:00, May 1, 2013 | 00:00:00, May 10, 2013 |
| Li Er | 34816 | 20:00:00, May 7, 2014 | 00:00:00, May 20, 2014 |
| Zhang San | 29845 | 20:00:00, May 15, 2014 | 00:00:00, May 30, 2014 |
| Li Si | 55465 | 20:00:00, May 5, 2014 | 00:00:00, May 30, 2014 | and query results for condition 2:

| User name | User ID | Start time | End time |
|---|---|---|---|
| Li Si | 55465 | 09:18:00, Feb. 29, 2016 | 09:18:15, Mar. 6, 2016 |

If a calculation expression input control inputs: Count (condition 2)/Count(condition 1), it calculates the ratio of cases which have alpha-fetoprotein content greater than 25 μg/l and positive Hepatitis B surface antigen for two years to cases which simultaneously suffer from restlessness, insomnia, and dry mouth for more than one week. According to the above query results, condition 1 is satisfied in 4 time periods and condition 2 is satisfied in only 1 time period. Therefore, the calculation expression result display control displays ¼=0.25.

If the calculation expression input control inputs: Avg (condition 1, alpha-fetoprotein), it calculates an average of alpha-fetoprotein in the query results satisfying condition 1, and thus the calculation expression result display control displays 24.75. The complete statistics query command transmitted to the server by the statistics query module of the corresponding client is: identifier 1: state 1=(mental state==restlessness && sleeping state==insomnia && salivary secretion==dry mouth) condition 1: EndTime(state 1)−StartTime(state 1)>1 week return data: Avg(condition 1, alpha-fetoprotein).

The user information input module of the client is used for collecting basic information of users, and comprises a user name input control, a user unique identification input control, a birth date and time input control, a gender input control, a nationality input control, an ethnicity input control, an address input control, a religious belief input control, an occupation input control, a post input control, and a user information statistics result display control. In the user information input module, every time a user completes the input of one piece of information, one or more statistics results related to this information will be displayed at the user information statistics result display control. For example, after inputting occupational information, diseases and morbidity and the like which are highly related to this occupation will be displayed. Its implementation mechanism is to generate corresponding query statistics commands according to the input information, and obtain the statistics query results through the statistics query interface based on characteristic data and time logic of the server. The basic information of users collected by the user information input module here, such as gender and nationality, also belongs to user characteristic data.

The new user characteristic data module of the client is used for defining new user characteristic data, and comprises a characteristic data name input control, a characteristic data ID input control, a characteristic data description text input control, a characteristic data or characteristic data item management selection control, and corresponding sub-interfaces; if the characteristic data or characteristic data item management selection control is selected as characteristic data, the new characteristic data interface comprises a characteristic data sub-interface; if the characteristic data or characteristic data item management selection control is selected as characteristic data item management, the new characteristic data interface comprises a characteristic data item management sub-interface; the characteristic data item management sub-interface comprises an item adding button, an item deleting button, an item copying button, an item modifying button, and an item list; the item adding button is clicked to pop up a new characteristic data item control; the new characteristic data item control comprises a characteristic data item name input control, a characteristic data item ID input control, a characteristic data item description text input control, a characteristic data or characteristic data item management selection control, and corresponding sub-interfaces; the characteristic data sub-interface comprises a characteristic data type selection control and other controls corresponding to characteristic data types; the characteristic data type selection control comprises two kinds of options, i.e., numerical value and classifications; if the characteristic data type is selected as a numerical value, the characteristic data sub-interface further comprises corresponding controls of a numerical type control, a numerical range input control, and a unit selection control; and if the characteristic data type is selected as a classification, the characteristic data sub-interface further comprises a corresponding control of a type set input control.

If the characteristic data or characteristic data item management selection control is selected as characteristic data, it is used for creating simple characteristic data. Taking new characteristic data-ABO blood type as an example, "ABO blood type" is inputted to the characteristic data name input control. "365637002" is inputted to the characteristic data ID input control. This ID is from SNOMED CT, and IDs in this embodiment all adopt SCTID if the IDs are defined in SNOMED CT. "ABO blood classification" is inputted to the characteristic data description text input control. The characteristic data or characteristic data item management selection control is selected as characteristic data. A classification is selected at the characteristic data type selection control of the characteristic data sub-interface. The name and ID of each blood type, such as name "Type A", ID "112144000", name "Type B", ID "112149005", name "Type AB", ID "165743006", name "Type 0", and ID "58460004", are sequentially inputted to the type set input control of the characteristic data sub-interface.

If the characteristic data or characteristic data item management selection control is selected as characteristic data item management, it is used for creating characteristic data in a composite structure. Taking new characteristic data-blood pressure as an example, the name of the characteristic data is inputted as "blood pressure". The ID of the characteristic data is inputted as "75367002". The description text of the characteristic data is inputted as "systemic circulation arterial blood pressure". The characteristic data or characteristic data item management selection control is selected as characteristic data item management. The item adding button is clicked in the characteristic data item management sub-interface to pop up the new characteristic data item control. "Systolic pressure" is inputted to the characteristic data item name input control of the new characteristic data item control, "271649006" is inputted to the characteristic data item ID input control, "pressure of blood to artery during ventricular systole" is inputted to the characteristic data item description text input control, characteristic data is selected in the characteristic data or characteristic data item management selection control in this new data item, the characteristic data type selection control is selected as a numerical value, a floating-point number is inputted to the numerical type control, >0 is inputted to the numerical range input control, and the unit selection control is selected as a millimeter mercury column; and the item adding button is clicked again in the characteristic data item management sub-interface to pop up the new characteristic data item control. "Diastolic pressure" is inputted to the characteristic data item name input control of the new characteristic data item control, "271650006" is inputted to the characteristic data item ID input control, "pressure of blood to artery during ventricular diastole" is inputted to the characteristic data item description text input control, and other inputs in this new data item are the same as those involved in "systolic pressure" above.

The new non-characteristic data module of the client is used for defining new non-characteristic data, and comprises a non-characteristic data name input control, a non-characteristic data ID input control, a non-characteristic data description input control, and a non-characteristic data format set input control. Taking CT image as an example, "CT image" is inputted to the non-characteristic data name input control, "F211234001" is inputted to the non-characteristic data name input control, "computed tomography image" is inputted to the non-characteristic data description input control, and "DICOM" is inputted to the non-characteristic data format set input control. Taking a surgical video as an example, "surgical video" is inputted to the non-characteristic data name input control, "F34124002" is inputted to the non-characteristic data name input control, "surgical video" is inputted to the non-characteristic data description input control, and "MP4" and "AVI" are inputted to the non-characteristic data format set input control. Taking a blood test report picture as an example, "blood test report picture" is inputted to the non-characteristic data name input control, "F23452003" is inputted to the non-characteristic data name input control, "blood test report picture" is inputted to the non-characteristic data description input control, and "BMP" and "TIFF" are inputted to the non-characteristic data format set input control.

The new process module of the client is used for defining a new process, and comprises a process name input control, a process ID input control, a process description text input control, and a process characteristic data management control. The process characteristic data management control comprises a characteristic data adding button, a characteristic data deleting button, a characteristic data copying button, a characteristic data modifying button, and a characteristic data list; the characteristic data adding button is clicked to pop up a process characteristic data adding control; the process characteristic data adding control comprises a common process characteristic data list and a new process characteristic data button; the new process characteristic data button is clicked to pop up a new process characteristic data control; the new process characteristic data control comprises a process characteristic data name input control, a process characteristic data ID input control, a process characteristic data description text input control, a characteristic data type selection control, and other controls corresponding to characteristic data type selection; the characteristic data type selection control comprises two options, i.e., numerical value and classification; if the characteristic data type is selected as a numerical value, the process characteristic data sub-interface further comprises corresponding controls of a numerical type control, a numerical range input control, a numerical input control, and a unit selection control; and if the characteristic data type is selected as a classification, the process characteristic data sub-interface further comprises corresponding controls of a type set input control and a type selection control. In addition to displaying the name, ID, value, and unit of respective pieces of characteristic data, the characteristic data list further has a planned attribute changing selection box and an attribute recording selection box. When the planned attribute changing selection box is ticked, it indicates that the characteristic data can be changed when it is planned; and when the attribute recording selection box is ticked, it indicates that the characteristic data is data that needs to be recorded when recording is executed.

Taking a treatment plan of intravenously dripping cefotaxime sodium as an example, "treatment plan of intravenously dripping cefotaxime sodium" is inputted to the new process name input control, "Z23418004" is inputted to the process ID input control, and "intravenous drip of cefotaxime sodium" is inputted to the process description text input control. The characteristic data adding button on the process characteristic data management control is clicked, a medicine is selected from the common process characteristic data list on the pop-up process characteristic data adding control, and the finish button is clicked. Medicine characteristic data will appear in the process characteristic data list of the process characteristic data management control, and it is classification characteristic data. The name and ID of each medicine in the type set are from SNOMED CT. In the process characteristic data list, the name "cefotaxime sodium" and ID "41722006" are selected for the medicine characteristic data. The characteristic data adding button on the process characteristic data management control is continuously clicked, an action is selected in the common process characteristic data list on the pop-up process characteristic data adding control, and the finish button is clicked. Action characteristic data will appear in the process characteristic data list of the process characteristic data management control, and it is classification characteristic data. The name and ID of each action in the type set are from Action and Procedure acting on patients in SNOMED CT. In the process characteristic data list, the name "intravenous drip" and ID "41722006" are selected for the action characteristic data. The characteristic data adding button on the process characteristic data management control is continuously clicked, and the new process characteristic data button on the pop-up process characteristic data adding control is clicked. "Daily dosage" is inputted to the process characteristic data name input control of the pop-up new process characteristic data control, "260911001" is inputted to the process characteristic data ID input control, "daily dosage of medicine" is inputted to the process characteristic data description text input control, a numerical value is selected in the characteristic data type selection control, a floating-point number is inputted to the numerical type control, >0 is inputted to the numerical range input control, g is selected in the unit selection control, and the finish button is clicked. Dosage characteristic data will appear in the process characteristic data list of the process characteristic data management control, and it is a numerical characteristic data. In the process characteristic data list, a numerical value 3 is inputted for the dosage characteristic data, representing a dosage of 3 g per day. The characteristic data adding button on the process characteristic data management control is continuously clicked, and the new process characteristic data button is clicked on the pop-up process characteristic data adding control. "Treatment course" is inputted to the process characteristic data name input control of the pop-up new process characteristic data control, "228864003" is inputted to the process characteristic data ID input control, "duration of treatment" is inputted to the process characteristic data description text input control, a numerical value is selected in the characteristic data type selection control, an integer is inputted to the numerical type control, >0 is inputted to the numerical range input control, day is selected in the unit selection control, and the finish button is clicked. Treatment course characteristic data will appear in the process characteristic data list of the process characteristic data management control, and it is numerical characteristic data. A numerical value 10 is inputted for the treatment course characteristic data in the process characteristic data list, representing that the course of treatment is 10 days. The characteristic data adding button on the process characteristic data management control is continuously clicked, and the new process characteristic data button is clicked on the pop-up process characteristic data adding control. "Daily cost" is inputted to the process characteristic data name input control of the pop-up new process characteristic data control, "T8749029" is inputted to the process characteristic data I D input control, "daily cost for treatment" is inputted to the process characteristic data description text input control, a numerical value is selected in the characteristic data type selection control, a floating-point number is inputted to the numerical type control, >0 is inputted to the numerical range input control, Yuan is selected in the unit selection control, and the finish button is clicked. Treatment course characteristic data will appear in the process characteristic data list of the process characteristic data management control, and it is numerical characteristic data. A numerical value 100 is inputted for the cost characteristic data in the process characteristic data list, representing that the daily cost for treatment is 100 Yuan. Finally, the planned attribute changing selection boxes corresponding to the three pieces of characteristic data, i.e., daily dosage, course of treatment, and daily cost are selected in the characteristic data list and ticked, representing that the three attributes, i.e., daily dosage, course of treatment, and daily cost of this process can be changed when the process is planned; and the attribute recording selection boxes corresponding to the two characteristic data, i.e., daily dosage and daily cost are selected in the characteristic data list and ticked, representing that the two attributes, i.e., daily dosage and daily cost of this process are data that needs to be recorded when the process is executed. The creation process of new characteristic data will be described here by taking daily dosage, course of treatment, and daily cost as an example, and an administrator can configure a daily dosage, course of treatment, and daily cost into the common process data list.

The user characteristic data input module comprises a characteristic data name selection control, a characteristic data ID display control, a characteristic data description text display control, a characteristic data statistics result display control, a characteristic data or characteristic data item input control, and a corresponding characteristic data time input control and characteristic data time type selection control. Still taking blood pressure as an example, "blood pressure" is selected in the characteristic data name selection control, "75367002" is displayed in the characteristic data ID display control, and "systemic circulation arterial blood pressure" is displayed in the characteristic data description text display control. The characteristic data item input control comprises two characteristic data items, in which one characteristic data item name is displayed as "systolic pressure", the characteristic data item ID is displayed as "271649006", the characteristic data item description text is displayed as "pressure of blood to artery during ventricular systole", 140 is inputted to the numerical input control, and the unit is displayed as millimeter mercury column; and the other characteristic data item name is displayed as "diastolic pressure", the characteristic data item ID is displayed as "271650006", the characteristic data item description text is displayed as "pressure of blood to artery during ventricular diastole", 90 is inputted to the numerical input control, and the unit is displayed as millimeter mercury column. The time of measuring blood pressure is inputted to the characteristic data time input control. The characteristic data time type selection control is selected as "observation time". The characteristic data statistics result display control displays statistics results related to the input data, such as the ratio of systolic pressure greater than 140 mm mercury column, and this ratio data is obtained by the client performing query through the statistics query interface based on characteristic data and time logic of the server. Inputted to the characteristic data time input control is a time period. The characteristic data time type selection control can select whether the above time period is the effective time or observation time of the characteristic data.

The non-characteristic data input module of the client comprises a data name selection control, a data description text display control, a data statistics result display control, a data file selection control, a data time input or display control, and a time type selection control. Still taking CT image as an example, "CT image" is selected in the data name selection control; the description "computed tomography image" inputted when the new non-characteristic data is created is displayed in the data description text display control; a certain statistics result related to a CT image is displayed in the data statistics result display control; a CT image file that needs to be uploaded is selected in the data file selection control, and the format of the file is checked as DICOM format and the file is uploaded; and because the information of data collection time is contained in the CT image, the data time input or display control is a display control here, which directly displays the collection time of the CT image, and "observation time" is selected in the time type selection control.

The process decision support module performs decision support according to characteristic data and statistics information, and specifically performs the following three steps:

1) characteristic matching, i.e., matching current characteristic data with a great amount of recorded case characteristic data in the system to acquire a matched case set.

The characteristic data for matching is usually based on abnormal user characteristic data, such as temperature data above a normal value and a white blood cell count above a normal value. The characteristic data for matching may also comprise necessary non-abnormal user characteristic data. For example, for a lung cancer patient, the user characteristic data is: location (left lung), typing (non-small cell squamous cell carcinoma), and staging (T3N2M0). Because the age of the patient is also an important factor in the selection of treatment plan, it should be used as the necessary non-abnormal user characteristic data to participate in the matching. The characteristic data for matching may also comprise necessary process characteristic data. For example, for a patient with local progression of lung cancer, the user characteristic data is: location (left lung), typing (non-small cell squamous cell carcinoma), and staging (T2N2M0). Because whether or not radiotherapy is performed within 6 months will affect the follow-up treatment plan, it should be used as the necessary process characteristic data to participate in the matching.

That the characteristic data for matching can be individually configured means that for a group of abnormal characteristic data, the corresponding other characteristic data participating in the matching, the method for matching the characteristic data, and indexes to measure whether the characteristic data is matched all can be individually configured. For a group of abnormal characteristic data, the corresponding other characteristic data participating in the matching, such as the age of the patient in the above example, and whether or not radiotherapy is performed within 6 months, may be configured, by an administrator, according to a clinical pathway, to participate in the matching by default; or the characteristic data participating in the matching may be configured by the user, or it is configured that closely related characteristic data is automatically determined by a computer through regressive analysis to participate in the matching. There are many methods for matching characteristic data. The following two methods are listed here: a) converting numerical type characteristic data into classification type characteristic data, and then performing strict type matching, wherein the characteristic data time is effective when the time period is the same; and b) performing strict type matching on the classification type, and configuring different matching allowable differences for different numerical types, wherein the characteristic data time is effective when the maximum interval is smaller than a set value. Taking body temperature data and white blood cell count as an example, method a can divide body temperature data into three classifications, i.e., too low body temperature, normal body temperature, and too high body temperature by respectively taking 36° C. and 37° C. as boundaries, and divide white blood cell count into three classifications, i.e., too low white blood cell count, normal white blood cell count, and too high white blood cell count by taking $3.5*10^{9}/L$ and $9.5*10^{9}/L$ as boundaries, the characteristic data time is effective when it is on the same day, wherein 36° C. and 37° C. are indexes to measure whether the body temperature is matched, and $3.5*10^{9}/L$ and $9.5*10^{9}/L$ are indexes to measure whether the white blood cell count is matched; and the method b performs matching based on that the temperature difference is smaller than 0.3° C. and the white blood cell count difference is smaller than $1.0*10^{9}/L$, the characteristic data time is effective when the maximum interval is smaller than 24 hours, wherein 0.3° C. is an index to measure whether the body temperature is matched, and $1.0*10^{9}/L$ is an index to measure whether the white blood cell count is matched. For example, one piece of user characteristic data is: temperature (39.1° C.) characteristic data time (from 14:45:00, Dec. 16, 2016 to 14:50:00, Dec. 16, 2016), white blood cell count ($11.4*10^{9}/L$) characteristic data time (from 12:45:00, Dec. 16, 2016 to 12:45:15, Dec. 16, 2016). When the matching is performed according to method a, the patient has too high body temperature and too high white blood cell count, all the characteristic data time of body temperature and white blood cell count is on the same day (rule for converting observation time to effective time), and cases with too high body temperature and too high white blood cell count are matching items; when the matching is performed according to method b, the interval of all the characteristic data time of body temperature and white blood cell count is smaller than 24 hours (rule for converting observation time to effective time), and cases with body temperature between 38.8° C. and 39.4° C. and white blood cell count between 10.4*10^9/L and 12.4*10^9/L are matching items. For different types of characteristic data combinations, the administrator can configure default matching methods and matching indexes; and the user can also configure individualized matching methods and matching indexes. The matching is completed through the statistics query interface based on characteristic data and time logic.

2) Process classification and statistics evaluation, i.e., classifying the matched case set according to processes to be further adopted, and performing statistics evaluation on each process classification. The processes to be further adopted refer to examination to be further adopted, treatment, or environmental changes affecting users under the situation that the matched characteristic data is known. That the indexes for evaluation can be individually configured means that for a set of matched characteristic data and processes, different evaluation indexes can be individually configured for statistics evaluation. For example, for a suspected lung cancer patient, the characteristic data is: do you cough (yes), do you cough up blood (yes), whether there is a pulmonary shadow in an X-ray chest film (yes), CEA (10 ng/ml), NSE (36 ng/ml), and CYFRA21-1 (33 ng/ml). The processes to be further adopted in the case set obtained by means of matching according to the above characteristic data comprise CT examination, MR examination, PET-CT examination, etc. A cure rate, ECOG score average after treatment, KPS score average after treatment, three-year progression-free survival rate and the like may be configured as evaluation indexes, i.e., the examination may be evaluated by comparing the quality of life and treatment effect of patients in the case set treated with different examinations. For another example, for an early lung cancer patient, the characteristic data is: location (right lung), typing (non-small cell squamous cell carcinoma), and staging (T1N1M0). The processes to be further adopted comprise stereotactic radiotherapy and wedge excision. A five-year cancer specific survival rate, five-year overall survival rate, five-year recurrence rate, cost and the like may be configured as evaluation indexes. Certain combined indexes may also be configured as evaluation indexes. For example, a weighted combined index of survival rate and cost can reflect treatment effect and cost at the same time. The above evaluation results are completed through the statistics query interface based on characteristic data and time logic.

3) Process recommendation, i.e., generating a recommended process list according to classification evaluation results and recommendation rules. That recommendation rules can be individually configured means that for a group of matched characteristic data and processes, the ranking indexes, ranking method, and display rules of the recommended process list can be individually configured. The number of times that a process is selected and executed can be used as a default ranking index, i.e., it is considered that the process which is selected for the most times is the most reasonable. The ranking indexes such as five-year survival rate, five-year recurrence rate, cure rate, and average healing time may also be individually configured. The ranking method may be ascending and descending. The display rules may be to set the number of recommended items. The administrator may configure recognized evaluation indexes, ranking method, and display rules for certain characteristic data and processes as default, and the user may also individually configure them.

The process planning and execution module of the client may select from the above recommended processes or specify other processes for planning. It comprises a process name display control, a process ID display control, a process description text display control, a process characteristic data display and modification control, and a process planning and execution control. The process planning and execution control is used for setting the time planning of process execution, and recording the actual characteristic data values and execution time during process execution.

Still taking "treatment plan of intravenously dripping cefotaxime sodium"as an example, the process name display control displays" treatment plan of intravenously dripping cefotaxime sodium", the process ID display control displays "Z23418004", the process description text display control displays "intravenous drip of cefotaxime sodium", and the process characteristic data display and modification control displays 4 pieces of characteristic data respectively as: medicine (cefotaxime sodium), action (intravenous drip), daily dosage (3 g), course of treatment (10 days), and daily cost (100 Yuan). Because when the new process module creates this process, the daily dosage, course of treatment, and daily cost characteristic data is configured to be changeable when it is planned, the user can change the values of daily dosage, course of treatment, and daily cost when necessary. The course of treatment is arranged in the process planning control, and consecutive 10 days starting from a certain date are selected in the date and time control. Because when the new process module creates this process, the daily dosage and daily cost characteristic data is configured as data to be recorded, when a certain execution date is clicked on the date and time control, the actual dosage, cost, and process execution time on this day can be recorded.

When the examination process is recorded, its execution time is effective time. When the examination results are inputted as characteristic data, the corresponding execution time of the examination process might be observation time (such as white blood cell count in blood test).

Figure 2:
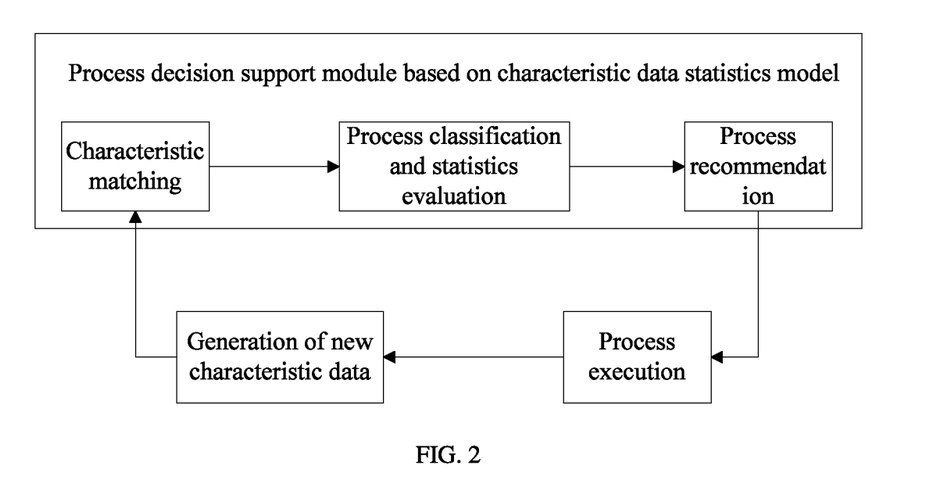
FIG. 2 illustrates a work flowchart of a process decision support module.

After the process execution is accomplished, further user characteristic data can be obtained for further decision. The workflow of the whole process decision support is as illustrated in FIG. 2.

The non-characteristic data processing interface in this embodiment comprises a non-characteristic data query interface, an interface for acquiring non-characteristic data from the personal health record system, and an interface for transmitting characteristic data extracted from the non-characteristic data and newly generated non-characteristic data back to the personal health record system. Herein, the non-characteristic data query interface comprises non-characteristic data query command definitions and returned query result data definitions. The interface for acquiring non-characteristic data from the personal health record system comprises non-characteristic data request definitions and non-characteristic data transmission definitions. The interface for transmitting characteristic data extracted from the non-characteristic data back to the personal health record system comprises characteristic data writing command definitions.

The non-characteristic data processing side transmits the non-characteristic data query command according to the definition. After receiving the command, the server queries the database according to the command, and then transmits the query result data back to the non-characteristic data processing side according to the defined format. The non-characteristic data query command comprises a non-characteristic data name or ID that indicates an object to be queried, query conditions that filter qualified records from query objects, and return data that indicate data items to be returned in the qualified records. For example, when a CT sequence of all patients with surname Huang who underwent CT scanning in hospital A on May 5, 2016 is queried, the data that needs to be returned are patient name, patient ID, and CT sequence ID. The query command is "non-characteristic data name: CT sequence; condition: hospital name==A && process name==CT scanning && scanning date=May 5, 2016 && name==Huang *; return data: name, patient ID, CT sequence ID". In this way, the non-characteristic data processing side should receive a list of names, patient IDs, and CT sequence IDs corresponding to all qualified CT sequences. The user of the non-characteristic data processing side may select the needed non-characteristic data from the returned query data list, transmit a non-characteristic data request to the server according to the definition, read the corresponding non-characteristic data from the database according to the request after receiving the request, and transmit the non-characteristic data to the non-characteristic data processing side according to the definition. For example, the non-characteristic data request is a CT sequence with CT sequence ID of 32435, and the request command is "CT sequence ID==32435 && object==CT sequence". After receiving this request, the server read the CT sequence with CT sequence ID of 32435 from the database and transmits it back to the non-characteristic data processing side. After the non-characteristic data processing side receives the CT sequence, the user of the non-characteristic data processing side may perform characteristic extraction on the CT sequence, such as draw tumor outline and calculate tumor volume. Finally, the acquired tumor volume is taken as characteristic data. A characteristic data writing command is transmitted to the server according to the definition. The command is "CT sequence ID=32435, characteristic data name=tumor volume, characteristic data ID=258261001, characteristic data value=125, characteristic data unit=cubic centimeter, start time=14:25:00, May 5, 2016, end time=14:25:01, May 5, 2016, time type=observation time", and it is transmitted back to the server. Here the real world time of the characteristic data "tumor volume" is from the image collection time contained in the non-characteristic data CT image, which is observation time.

Sometimes it is complicated to extract the real world time from the non-characteristic data. For example, considering the situation that the disease condition record described by natural language is used as the non-characteristic data, usually, the disease condition record time will be saved, but the disease condition record time is only benchmark time. The real world time of the characteristic data described in the disease condition record also depends on the explicit or implicit time expression corresponding to the characteristic data in the context, such as "yesterday" and "10 a.m. today". This involves natural language understanding and time extraction, and possibly only part of the characteristic data and corresponding real world time can be extracted. Because the system requires that the real world time of the user characteristic data and process execution must be received at the same time as receiving the user characteristic data and the process execution characteristic data, the characteristic data for which the corresponding real world time has not been extracted cannot be transmitted back to the server for saving.

For the definitions of symptom names, medicine names, data names, data ranges, medical operations, and units, a reference should be made to uniform standards to ensure data consistency. For example, a reference is made to SNOMED CT (Systematized Nomenclature of Medicine—Clinical Terms).

The invention claimed is:
1. A personal health record system with a process decision support function, wherein the system comprises a client and a server;
   the server is configured for non-characteristic data processing and statistics query based on characteristic data and time logic, wherein the non-characteristic data processing comprises non-characteristic data query, acquiring the non-characteristic data from the personal health record system, and transmitting characteristic data extracted from the non-characteristic data acquired from the personal health record system and newly generated non-characteristic data back to the personal health record system;
   the system is configured for performing:
   step 1: characteristic matching, comprising matching current characteristic data with recorded case characteristic data to acquire a matched case set;
   step 2: process classification and statistics evaluation, comprising classifying the matched case set according to processes to be further adopted, and performing statistics evaluation on each process classification;
   step 3: process recommendation, comprising generating a recommended process list according to classification evaluation results and recommendation rules,
   wherein the characteristic data comprises numerical variables and classification variables which reflect user information or process information, have a clinical significance, and have clear and consistent definitions; the non-characteristic data is other data except the characteristic data; the processes refer to diagnosis and treatment or environmental changes that affect users; and numerical variable characteristic data has clear and consistent data meanings, value ranges and units, and classification variable characteristic data has clear and consistent classification criteria and type set definitions,
   wherein the system is further configured for performing:
   receiving, from the client, non-characteristic data;
   receiving, from the client, characteristic data, wherein receiving characteristic data comprises simultaneously receiving real world time and time type corresponding to the characteristic data, and the time type is effective time or observation time, wherein the system comprises a rule for converting observation time into effective time;
   extracting, at the server, characteristic data from the non-characteristic data; and
   performing the characteristic matching in step 1 based on the received characteristic data, the characteristic data extracted from the non-characteristic data,
   wherein the client is further configured for performing:
   setting, based on a process in the recommended process list generated by the system, time planning of the process,
   executing the process, and
   recording actual characteristic data and execution time during process execution;

wherein the system is further configured for performing:
collecting the actual characteristic data generated at the client to the system for additional characteristic matching.

2. The personal health record system with a process decision support function according to claim 1, wherein the non-characteristic data processing further comprises user authorization and service purchase.

3. The personal health record system with a process decision support function according to claim 1, wherein the client is configured for user characteristic data input, user non-characteristic data input, process decision display;
wherein user characteristic data comprises basic information of users, symptoms, signs, inspection and examination results, clinically significant characteristics extracted from images, voices, videos, and waveform data of users, and all quantitative or classification data which reflect attributes or physical states of users and have clear and consistent definitions.

4. The personal health record system with a process decision support function according to claim 1, wherein the client is further configured for managing user information, user characteristic data, user non-characteristic data, and process data.

5. The personal health record system with a process decision support function according to claim 1, wherein current characteristic data participating in the matching in step 1, evaluation indexes for the statistics evaluation in step 2, and the recommendation rules in step 3 all can be individually configured.

6. The personal health record system with a process decision support function according to claim 1, wherein the characteristic data comprises user characteristic data and process characteristic data.

7. The personal health record system with a process decision support function according to claim 1, wherein the current characteristic data for matching in step 1 comprise abnormal user characteristic data, necessary non-abnormal user characteristic data, and necessary process characteristic data.

8. The personal health record system with a process decision support function according to claim 1, wherein the matching in step 1 is completed based on characteristic data and time logic.

9. The personal health record system with a process decision support function according to claim 1, wherein the statistics evaluation in step 2 is completed based on characteristic data and time logic.

10. The personal health record system with a process decision support function according to claim 1, wherein the client is configured for statistics query, user information input and process execution.

* * * * *